(12) United States Patent
Raylman

(10) Patent No.: US 10,384,019 B2
(45) Date of Patent: Aug. 20, 2019

(54) SYSTEMS AND METHODS FOR AUTOMATICALLY ADJUSTING NEEDLE PENETRATION DEPTH FOR AUTO-INJECTOR DEVICES

(71) Applicant: West Virginia University, Morgantown, WV (US)

(72) Inventor: Raymond R. Raylman, Morgantown, WV (US)

(73) Assignee: West Virgina University, Morgantown, VA (US)

(*) Notice: Subject to any disclaimer, the term of this patent is extended or adjusted under 35 U.S.C. 154(b) by 118 days.

(21) Appl. No.: 15/482,065

(22) Filed: Apr. 7, 2017

(65) Prior Publication Data

US 2017/0290995 A1    Oct. 12, 2017

Related U.S. Application Data

(60) Provisional application No. 62/401,567, filed on Sep. 29, 2016, provisional application No. 62/321,391, filed on Apr. 12, 2016.

(51) Int. Cl.
*A61M 5/46* (2006.01)
*A61M 5/20* (2006.01)

(52) U.S. Cl.
CPC ............. *A61M 5/46* (2013.01); *A61M 5/20* (2013.01); *A61M 2005/206* (2013.01); *A61M 2005/2013* (2013.01); *A61M 2205/332* (2013.01); *A61M 2205/584* (2013.01)

(58) Field of Classification Search
CPC .......... A61B 5/150175; A61B 5/15019; A61B 5/150198; A61M 5/46
See application file for complete search history.

(56) References Cited

U.S. PATENT DOCUMENTS 6,213,977 B1    4/2001  Hjertman et al.
2005/0163711 A1    7/2005  Nycz et al.

FOREIGN PATENT DOCUMENTS

WO    2015/131903 A1    9/2015

OTHER PUBLICATIONS

Scheiner, Gary, "Injection Aids to the Rescue!"; BD Diabetes (BD.com) Diabetes Learning Center, May 2007.

*Primary Examiner* — Emily L Schmidt
(74) *Attorney, Agent, or Firm* — Thomas | Horstemeyer, LLP

(57) ABSTRACT

Disclosed are various embodiments of an auto-injector device that automatically and dynamically adjusts the depth that a needle will penetrate into a target area of the body. In one embodiment, the auto-injector device includes the needle being moveably disposed within a needle housing. The auto-injector device further includes a needle depth estimator having a needle depth limiter that extends into an inner portion of the needle housing and is designed to engage with a needle stop of the needle and restrict downward movement of the needle. The needle depth estimator can automatically adjust a position of the needle depth limiter within the needle housing according to movement of a compression mechanism surrounding a lower portion of the needle housing.

20 Claims, 13 Drawing Sheets

SYSTEMS AND METHODS FOR AUTOMATICALLY ADJUSTING NEEDLE PENETRATION DEPTH FOR AUTO-INJECTOR DEVICES

CROSS-REFERENCE TO RELATED APPLICATIONS

This application is a continuation of U.S. utility application entitled, "Intelliject: A Device and Method for the Automatic Determination and Setting of Needle Penetration Depth for Auto-Injectors," having application No. 62/321,391, filed Apr. 12, 2016, and "Intelliject: A Device and Method for the Automatic Determination and Setting of Needle Penetration Depth for Auto-Injectors: Addendum Describing a Method for Adjusting the Device for Individual Users," having application No. 62/401,567, filed Sep. 29, 2016, both of which are entirely incorporated herein by reference.

BACKGROUND

The injection of pharmaceuticals by non-medically trained individuals is a growing trend. Typical injector devices deliver a predetermined amount of drug to the patient. Auto-injectors are most often used by 1) people who must administer a drug on an emergency basis (e.g., epinephrine to counter a serious allergic reaction) or 2) people who must administer a drug on a regular basis where repeated visits to a health care professional are not practical (e.g., insulin to control glucose levels in diabetics).

SUMMARY

Included are various embodiments of systems and methods related to an auto-injector device that automatically and dynamically adjusts the depth that a needle will penetrate into a target area of the body. One embodiment of a system, among others, includes an auto-injector device comprising a needle; a needle housing, the needle being moveably disposed within the needle housing; a compression mechanism surrounding a lower portion of the needle housing; and a needle depth estimator coupled to the compression mechanism, the needle depth estimator comprising a needle depth limiter extending into an inner portion of the needle housing and being designed to engage with a needle stop of the needle and restrict downward movement of the needle, and the needle depth estimator being designed to automatically adjust a position of the needle depth limiter within the needle housing based at least in part on movement of the compression mechanism about the needle housing.

Another embodiment of a system, among others, includes an auto-injector device comprising a first tube; a second tube being moveably disposed around the first tube in a telescoping arrangement, the second tube being situated about a lower portion of the first tube; a compression mechanism disposed around the first tube and adjacent to a top end of the second tube, the compression mechanism being designed to transmit the force applied to the second tube to the first in such a way that the applied force is fed back to the user and used to assist in setting needle depth; and a depth estimation mechanism coupled to the second tube, the depth estimation mechanism comprising a position indicator extending into an inner portion of the first tube, and the depth estimation mechanism being designed to adjust a position of the position indicator based at least in part on movement of the second tube.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
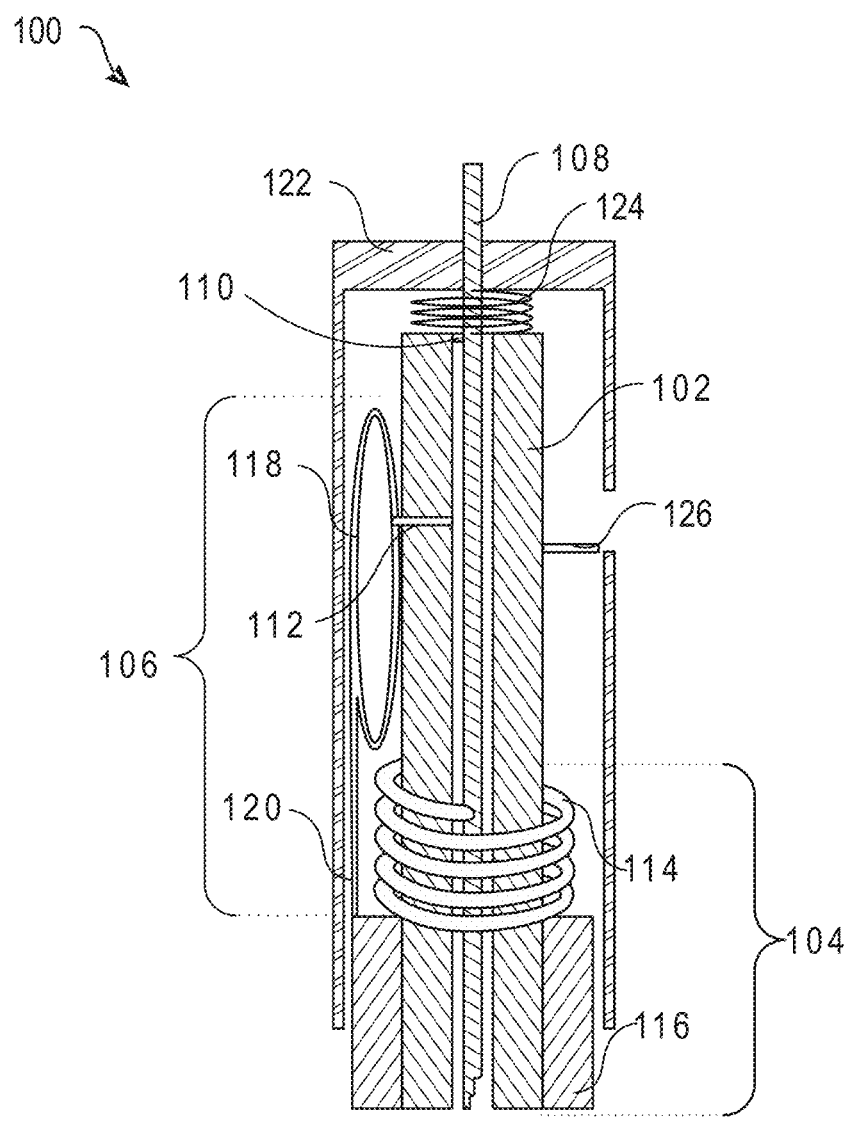
FIG. 1 is a drawing of an example of a cross section of an auto-injector device according to various embodiments of the present disclosure.

Disclosed herein are various embodiments of systems and methods related to an auto-injector device that automatically and dynamically adjusts the depth that a needle will penetrate into a target area of the body. Specifically, the auto-injector device of the present disclosure responds to the softness of a target area when pressed upon a target area of the body. Different levels of softness of the target area can be interpreted by the auto-injector device as different depths of fat tissue to be penetrated. Since the auto-injector device of the present disclosure automatically sets the depth of needle penetration, a user can administer injectable pharmaceuticals, for example, using the auto-injector device without prior knowledge and/or a predefined setting of the required injection depth.

While the amount of drug delivered is important in auto-injector devices, it is also critical that the drug is delivered to the target tissue (e.g., muscle). If the injection is not administered properly, the effect of the drug may be minimized or nullified. The problem is that in most areas of the body there is a layer of fat between the skin and target tissue, and there is often some bony structure beneath the muscle. As such, the needle must penetrate the target area deep enough to reach muscle through the fat, but not too deep to where it will strike bone. The thickness of fat layer is dependent upon injection site and individual body composition.

To address the dosage issue, auto-injector manufacturers can load known devices with a fixed amount of drugs appropriate for the intended use and/or patient, or permit the dose to be adjusted by a setting on the injector. The depth question is more complex because fat depth varies from person-to-person, is different for various areas of the body, and can change over time as the body mass of a patient changes. Known auto-injector devices typically have a fixed needle length or a manual adjustment to change needle depth. In other words, versions of known auto-injector devices either lack adjustable depths (i.e., fixed length) or have manual depth adjustments that must be set by the user in consultation with a health care professional. Thus, unless the proper depth is determined prior to use by a health care professional, there is a possibility that the drug will not be administered properly. This problem is particularly important for auto-injectors devices that are meant to be used in emergencies to counter an unexpected event (e.g., allergic reaction) where the physical characteristics of the user is not known prior to application.

To address the problem of setting correct needle penetration depth, the auto-injector device of the present disclosure is designed to automatically and dynamically adjust needle depth as it is used (e.g., for a particular person, for a particular target area, etc.) based in part on an estimation of the softness of the target area of the body being penetrated. Specifically, needle penetration depth is determined and set at the time of each use. Therefore, a predefined needle depth or preset setting is not necessary as the automatic and dynamic adjustment feature of the auto-injector device permits effective use by any user without prior knowledge about how deep the needle must penetrate.

In the following discussion, a general description of the auto-injector device of the present disclosure and its components is provided, followed by a discussion of the operation of the same.

With reference to FIG. 1, shown is a drawing of an example of a cross section of the auto-injector device 100 according to various embodiments of the present disclosure. The auto-injector device 100 comprises a needle housing 102, a compression mechanism 104, a depth estimator mechanism 106, a needle 108, a needle stop 110, and a needle depth limiter 112, and an outer sleeve 122 and/or any other appropriate component. The needle 108 is movably disposed within the needle housing 102. In various embodiments, the needle 108 is fluidly connected to a fluid housing configured to contain fluid (e.g., medication) as can be appreciated. The needle housing 102 may comprise a tubular component comprising aluminum, acrylic, and/or any other suitable material. The compression mechanism (such as a spring) 104 is disposed around a bottom portion of the needle housing in a telescoping arrangement.

The compression mechanism 104 comprises a compression component 114 coupled adjacent to a top portion of a compression sleeve 116. The compression sleeve 116 may comprise a tubular component comprising aluminum, acrylic, and/or any other suitable material. The compression component 114 comprises a spring and/or any other suitable device that can establish a force to resist movement of the compression sleeve 116 along the needle housing 102 in an upward direction towards a top portion of the needle housing 102. In some embodiments, the compression constant of the compression component 114 can be adjusted to change the sensitivity of the amplitude of the deflection as a function of compression.

The depth estimator mechanism 106 comprises an adjusting component 118 that is designed to adjust the needle depth based at least in part on a movement of the compression mechanism. Specifically, the adjusting component 118 converts an upward thrust corresponding to the compression mechanism 104 into a downward deflection of the needle depth limiter 112 which extends outwardly from the depth estimator mechanism 106 and into a portion of the needle housing 102. As discussed in further detail below, the needle depth limiter 112 is designed to limit the amount of downward movement of the needle 108 disposed within the needle housing 102, thereby controlling the depth in which the needle 108 penetrates. The depth estimator mechanism 106 further comprises a connector component 120 connecting the adjusting component 118 to the compression sleeve 116 such that movement of the compression sleeve 116 causes the adjusting component 118 to convert an upward thrust of the compression sleeve into a downward deflection of the needle depth limiter 112.

In one non-limiting example, the adjusting component 118 may comprise a loop material disposed around two adjacent pulley components that are coupled to a portion of the needle housing 102. In this example, the upward movement of the compression sleeve 116 causes the loop to rotate about the pulleys causing the extending needle depth limiter 112 to move downward.

The needle depth limiter 112 extends outwardly from a portion of the adjustment component 118 and extends into a portion of the needle housing 102 allowing a portion of the needle depth limiter 112 to be positioned within an inner portion of the needle housing 102. For example, the needle housing 102 may comprise a slot (not shown) extending along a longitudinal axis of the needle housing 102. The depth estimator mechanism 106 can be situated about the needle housing 102 such that the needle depth limiter 112 extending outwardly from the portion of the adjustment component 118 is disposed within the slot of the needle housing 102. The needle depth limiter 112 is designed to engage with a needle stop 110 coupled to the needle 108 disposed within the needle housing 102 stopping further downward movement of the needle 108 about the longitudinal axis of the needle housing 102. The position of the needle depth limiter 112 with respect to the auto-injector device 100 is used to set the depth that the needle 108 will penetrate within a target area for releasing fluid within a body. As such, upon engagement with the needle depth limiter 112, the needle 108 is prevented from further downward movement, thereby controlling the depth that the needle 108 penetrates into a target area. In some embodiments, the depth estimator mechanism 106 can be calibrated to adjust the needle depth limiter 112 so the needle insertion depth will pass through subcutaneous fat and penetrate muscle. Depth is controlled so that it will not strike bone.

The outer sleeve 122 comprises a shell that encloses the remaining components of the auto-injector device 100 (e.g., needle housing 102, compression mechanism 104 (partially), depth estimator mechanism 106, etc.) with the exception of a portion of compression shell so that during compression, the dose of fluid released by the needle 108 does not come into contact with the surface. The outer sleeve 122 is the component that a user will hold during deployment of the auto-injector device 100.

The auto-injector device 100 may further comprise one or more compression components 124 that are disposed between and connect a top of the needle housing and an inner top portion of the outer sleeve 122. The compression components 124 may comprise one or more springs and/or any other appropriate component that can convert the downward motion of the force applied by a user to top portion of the outer sleeve 122 to the needle housing 102. In some embodiments, the compression constant of the components 124 can be adjusted to change the sensitivity of the amplitude of the deflection as a function of compression.

In some embodiments, the auto-injector device 100 may further comprise a gauge mechanism 126 that is designed to gauge the downward force applied to the auto-injector device 100. Specifically, the gauge mechanism 126 provides feedback to a user regarding the amount of force being applied. Since some minimum amount of force is required for proper operation of the auto-injector device 100, it is necessary to inform the user whether the minimum force threshold has been met. In some embodiments, the gauge mechanism 126 comprises an indicator that is visible to the user that moves proportional to the applied force. The indicator may move inside a coded (e.g. color) housing (not shown). Once the indicator moves into a particular area (e.g., green area), the user may know that is now safe to deploy the needle 108. Alternatively, an automated needle deployment system could be activated once sufficient force has been applied. Additionally, the gauge mechanism 126 gauges the force that the user is applying, which is important since the deflection of the compression sleeve 116 is partially related to the force applied to the needle housing 102. As such, in various embodiments, the needle penetration depth is determined by both the deflection of the compression sleeve 116 and the deflection of the gauge mechanism.

It should be appreciated that the sensitivity of the auto-injector device 100 to downward force (e.g., the amount of deflection of the needle depth limiter 112, the gauge mechanism 126, and/or ultimate determination of needle penetration depth) can be adjusted by adjusting the force constants of the compression components 124, the compression component 114, and/or the diameter of the thrust ring associated with the bottom of the compression sleeve 116. The ability to adjust the sensitivity allows for calibration of the auto-injector device 100 during optimization of the device and to account for indirect applications (e.g., application through clothing).

Next, a general description of the operation of the various components of the auto-injector device 100 is provided. The auto-injector device 100 of the present disclosure adjusts the penetration depth of a needle 108 based on an estimate of the thickness of the subcutaneous fat between the needle and muscle tissue at the target area of the body. The auto-injector device 100 is designed to measure the retraction of the compression mechanism 104 that is disposed around the needle housing 102 to determine the appropriate position of the needle depth limiter 112 within the needle housing 102. This task is accomplished by pressing the auto-injector device 100 against the skin at the target area. The pressure of the auto-injector device 100 against the skin forces the compression sleeve 116 to move in an upward position about the needle housing 102, thereby compressing the compression component 114 coupled to the top portion of the compression sleeve 116 upwards. The thicker the fat layer, the softer the tissue, which produces a greater motion of the needle housing 102 into the tissue as pressure is applied. This greater penetration of the needle housing 102 results in a greater upward motion of the compression sleeve 116. This upward motion is used by the depth estimator mechanism 106 to adjust the position of the needle depth limiter 112 (i.e., the larger the upward motion of the compression sleeve 116, the further down the needle depth limiter 112 is moved). When the needle 108 is inserted, its depth is controlled by the needle stop 110 striking the needle depth limiter 112.

Figure 2:
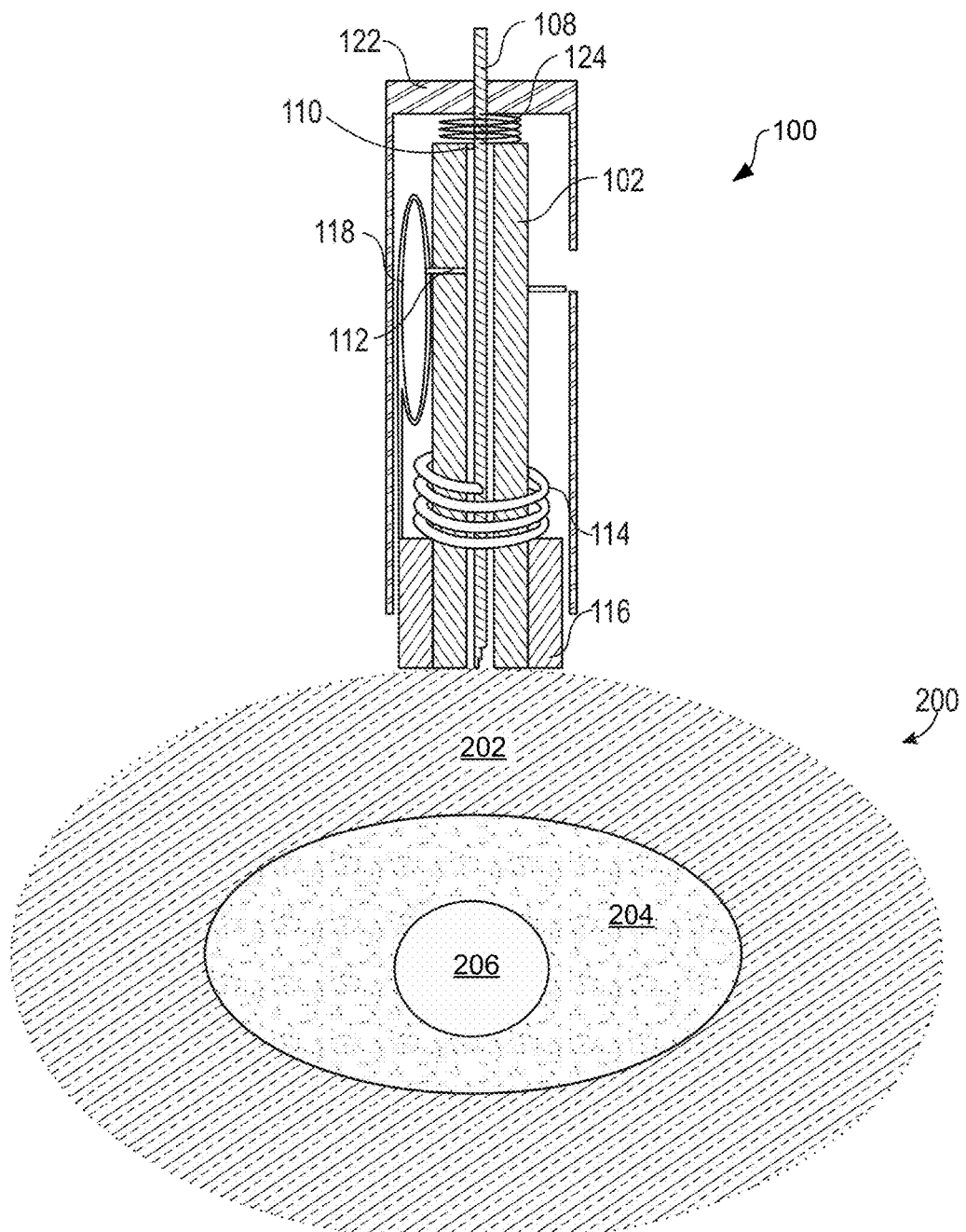
FIG. 2 is a drawing of an example of a cross section of the auto-injector device of FIG. 1 prior to compression against a target area of a body according to various embodiments of the present disclosure.

Turning now to FIG. 2, shown is an example of a cross section of the auto-injector device 100 positioned about a target area of a body according to various embodiments of the present disclosure. As shown in FIG. 2, the auto-injector device 100 is placed on the target area 200 where the compression sleeve 116 of the compression mechanism 104 is touching the target area 200. The target area 200 includes a fat region 202, a tissue region 204, and a bone region 206. As noted, since the auto-injector device 100 is not being pressed onto the target area 200, the compression sleeve 116 does not have an upward force applied to it. As such, the compression sleeve 116 is not compressed upward and the needle depth limiter 112 is in the originally set and calibrated position.

Figure 3:
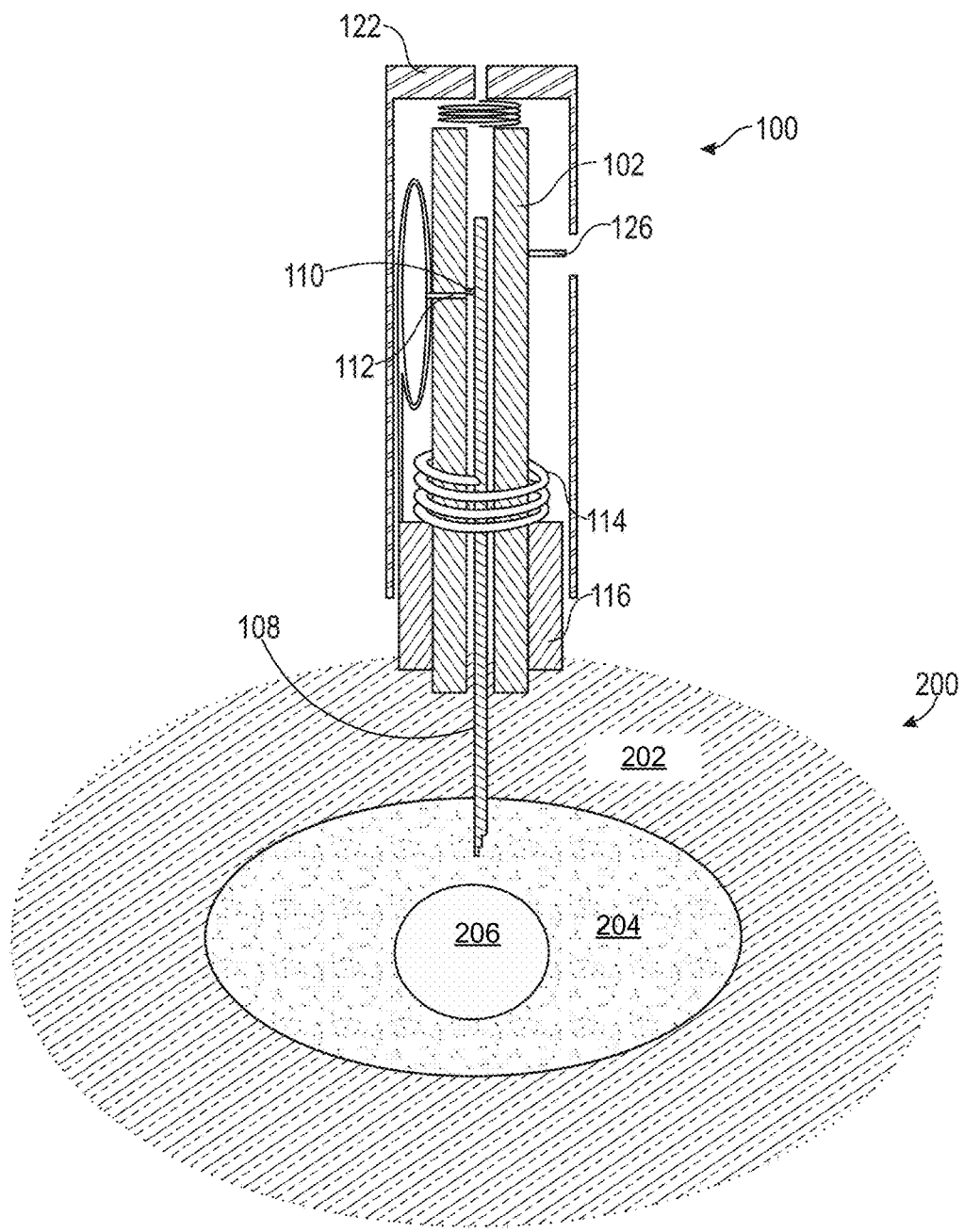
FIG. 3 is a drawing of an example of a cross section of the auto-injector device of FIG. 1 during use as compressed against a target area according to various embodiments of the present disclosure.

Referring next to FIG. 3, shown is an example of a cross section of the auto-injector device 100 following the deployment of the needle according to various embodiments of the present disclosure. In FIG. 3, the compression sleeve 116 of the compression mechanism 104 has moved upward about the needle housing 102 upon compression with the target area 200. As such, the upward movement of the compression sleeve 116 in turn causes the adjustment component 118 to convert the upward movement of the compression sleeve into a downward deflection of the needle depth limiter 112, thereby moving the needle depth limiter 112 to another position. As shown in FIG. 3, the needle stop 110 of the needle 108 is engaged with the needle depth limiter 112 thereby stopping further downward movement of the needle 108. Accordingly, the depth of the needle 108 is within the tissue region 204 of the target area 200 allowing for appropriate release of fluid into the tissue region 204. It should further be noted that the gauge mechanism 126 has deflected upward due to the force applied by the user providing feedback to the user that the force is sufficient for proper needle deployment. Further, the compression components 124 have been compressed in response to the applied force. This compression is responsible for transmitting the user-applied force to the needle housing 102. The deflection of the gauge mechanism 126 is also used in conjunction with the deflection gauged by the adjustment component 118 to set the correct needle penetration depth.

Figure 4:
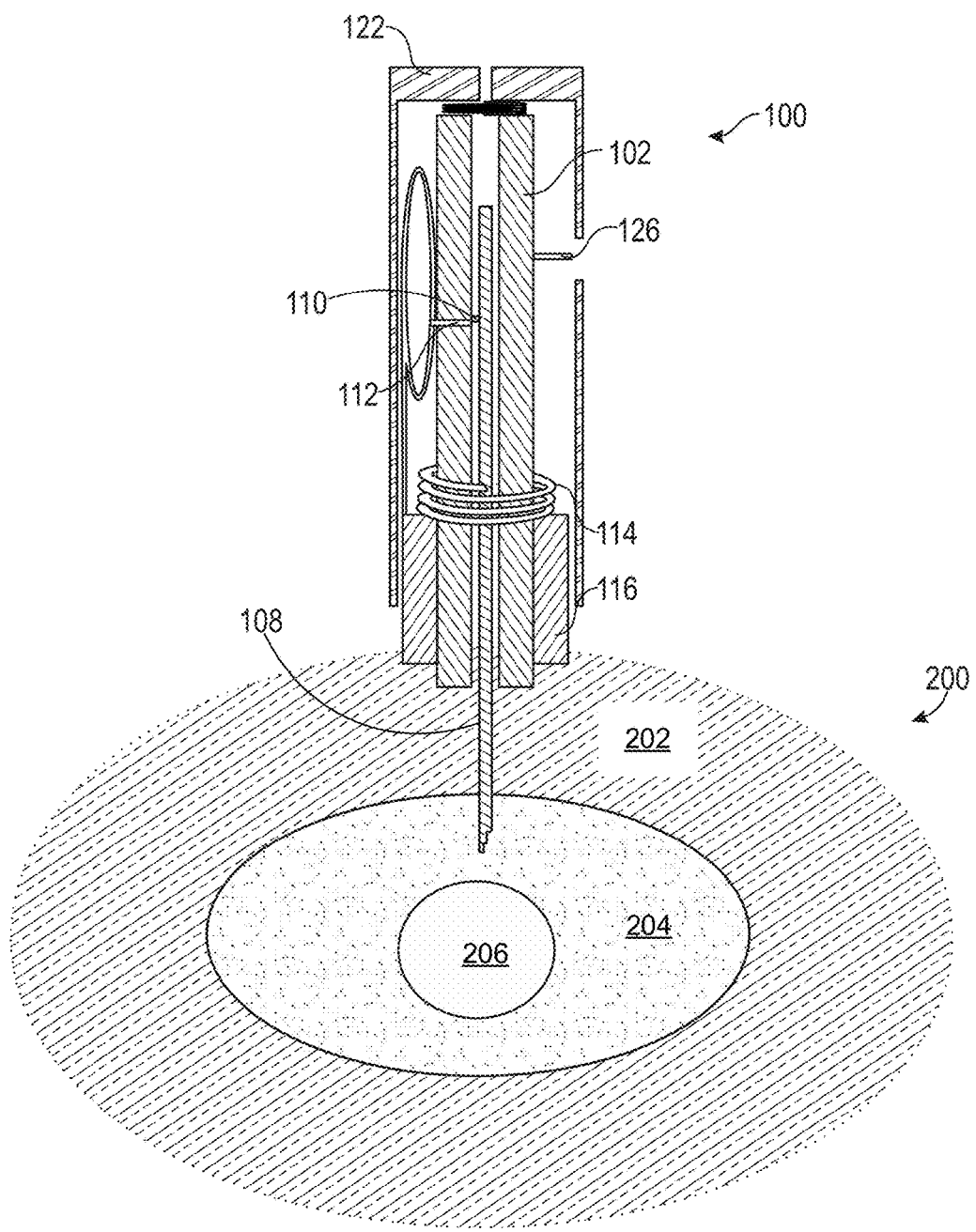
FIG. 4 is a drawing of an example of a cross section of the auto-injector device of FIG. 1 during use as compressed against a target area of a body that contains a thick subcutaneous fat region according to various embodiments of the present disclosure.

Moving on to FIG. 4, shown is an example of a cross section of the auto-injector device 100 being activated within a target area 200 of a body including a thick subcutaneous fat region 202 according to various embodiments of the present disclosure. As shown in FIG. 4, the compression component 114 is compressed greater than the compression component 114 of FIG. 3 due to the thicker fat region 202 of FIG. 4. Accordingly, the needle depth limiter 112 is moved further down the needle housing 102 allowing the needle 108 to extend deeper into the target area 200. As such, the needle depth accounts for the thicker fat region 202 and the needle 108 is placed in the appropriate region (e.g., the tissue region 204) for release of the fluid via the needle 108 into the target area 200 as can be appreciated.

In some embodiments, the non-compression position of the needle depth limiter 112 can be set to insert the needle 108 to a set depth. In some embodiments, the auto-injector device 100 can have a switch (not shown) to override the compression measurement and insert the needle 108 using the standard fixed depth method. This option can be provided if the compression measurement may be erroneous (e.g., insertion is performed through clothing).

An alternative embodiment to the mechanical means of determining the thickness of the subcutaneous fat layer and setting of the appropriate penetration depth comprises the use of a mini-ultrasound transducer (not shown) in the injector tip connected to a microprocessor. The fat region 202, the tissue region 204, and the bone region 206 can have very different ultrasound signatures. Therefore, the signals from the transducer can be processed by the microprocessor to determine the subcutaneous fat thickness and then set the needle depth limiter 112 appropriately.

An important aspect of the auto-injector device 100 is the capability to convert the upward motion of the compression sleeve 116, which is related to the softness of the tissue and thus the thickness of the fat region (or pad) 202, to the needle depth. To accomplish this task, an upward motion from the compression sleeve 116 can be converted into a downward motion of the needle depth limiter 112 to set the penetration depth of the needle 108. For example, a set of compound disks can be used to create a pulley system that converts upward motion to downward displacement. This configuration can also amplify the motion such that a small upward motion can result in a larger downward motion. The amount of amplification can be equal to the ratio of the diameters of the disks. By having a range of selectable disk diameters, the amplification can be adjusted by the user. This device can also be any type of mechanical or electromechanical element that converts upward motion to downward deflection with adjustable sensitivity.

Another embodiment of the auto-injector device 100 is presented with a dynamically-adjustable needle depth where deflection of the compression sleeve 116 can be used to set the needle insertion depth. The depth of the needle 108 can be varied for a given deflection of the compression sleeve 116 (based on fat pad thickness) by adjusting the amplification of the adjusting component (or deflection converter or compression encoder) 118. The adjustment capability of the depth estimator mechanism 106 permits the performance of the auto-injector device 100 to be optimized. It is possible for the user to adjust the sensitivity of the adjusting component 118 so that the needle 108 does not penetrate too far into the user, mitigating the possibility of striking an internal organ or bone. For example, if the device is to be used on a child, the maximum depth of the needle 108 should be smaller that if the user is an adult. An external switch can be used to adjust the deflection sensitivity by switching in or out a different set of compound disks with different amplification settings. In other embodiments, a variable gain deflection can be provided by a rack and pinion gear instead the compound disks.

Figure 5:
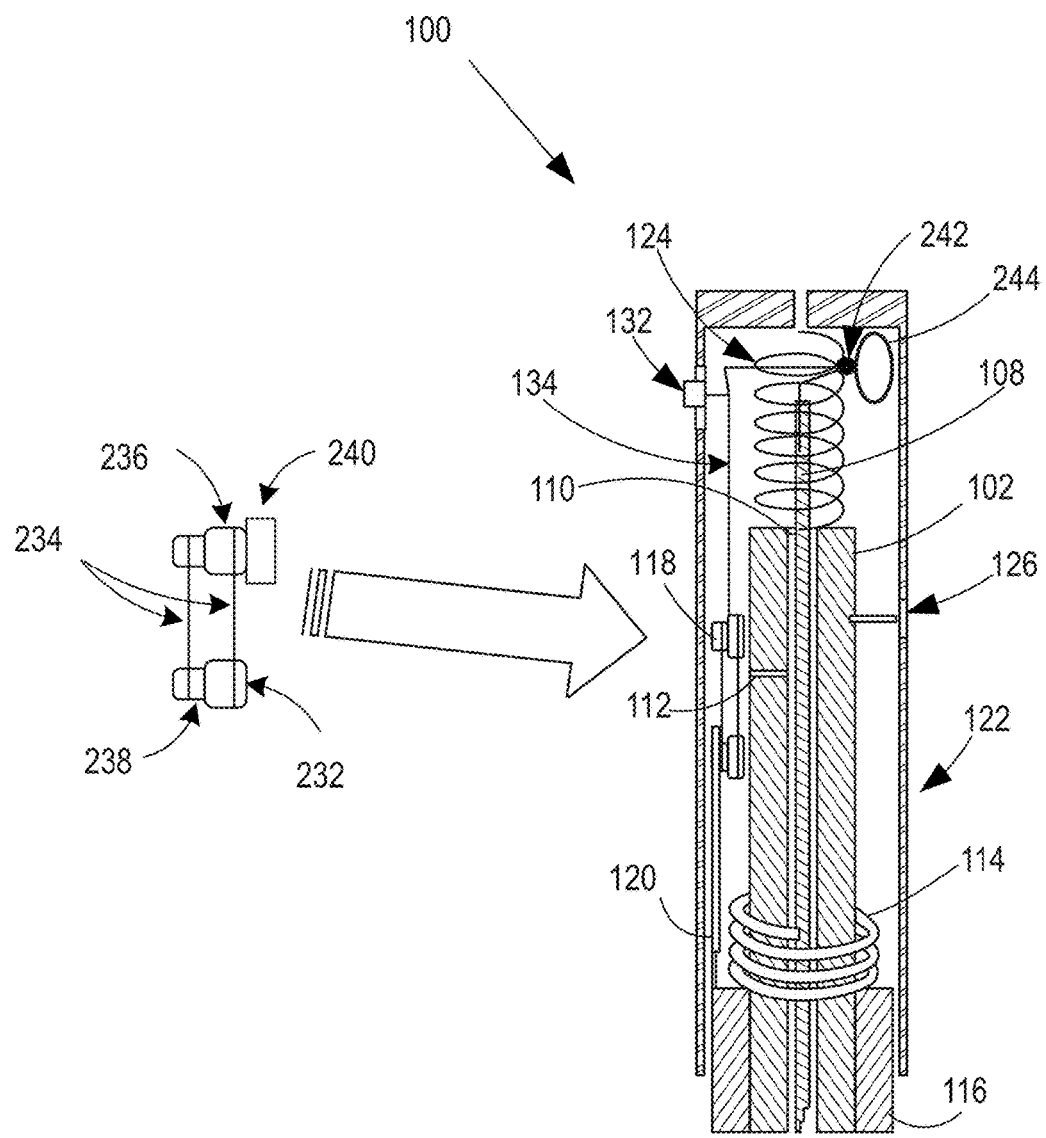
FIG. 5 is a drawing of another example of a cross section of an auto-injector device according to various embodiments of the present disclosure.

Referring to FIG. 5, shown is an example of an auto-injector device 100 having an adjusting component 118 comprising compound disks for adjustment of the deflection sensitivity. The auto-injector device 100 includes an outer sleeve 122 that a user can hold during deployment of the auto-injector device 100. The outer sleeve (or handle) 122 comprises a shell that can enclose the device 100, except for a portion of compression sleeve 116, so that during compression the outer sleeve 122 does not come in contact with the surface of the user. Compression components 124 (e.g., springs and/or any other appropriate component) can convert the downward motion of the force applied by the user to the needle housing 102 via a top portion of the outer sleeve 122.

The auto-injector device 100 comprises a gauge mechanism 126 to gauge the downward force applied to the auto-injector device 100. The gauge mechanism 126 provides feedback to the user regarding the amount of force they are applying. Since a minimum amount of force is needed for proper operation of the auto-injector device 100, the device 100 can inform the user whether this threshold has been met. Therefore, the gauge mechanism 126 monitors the amount of downward force exerted by the user and can provide feedback (visual, audio, etc.) as to whether sufficient pressure has been applied. In some embodiments, the gauge mechanism 126 can be in the form of an indicator (visible to that user) that moves proportionally to the applied force. The indicator can move inside, e.g., a color-coded housing. For example, when the indicator moves into a "green area" (a visual range that indicated the applied for is acceptable for needle deployment) the user knows that it is now safe to deploy the needle 108. In various embodiments, the gauge mechanism 126 can provide an audio signal that indicates whether sufficient pressure has been applied. Alternatively, an automated needle deployment system could be activated once sufficient force has been applied.

Additionally, gauge mechanism 126 can gauge the force that the user is applying, which is important since the deflection of the compression sleeve 116 is partially related to the force applied to the needle housing 102. Therefore, the needle penetration depth can be determined by the deflection of compression sleeve 116 and gauge mechanism 126. The gauge mechanism 126 may also be configured to prevent deployment of the needle 108 (e.g., through an interlock) until sufficient force has been applied.

As shown in FIG. 5, the auto-injector device 100 includes a switch 132 that can be used to set the sensitivity of the adjusting component (or thrust converter) 118 via an actuator 134 that interacts with the adjusting component 118. The switch 132 can be configured to select one of a plurality of different sensitivity settings (e.g., child, adult, obese, etc.). At the highest sensitivity setting, the deflection of the compression sleeve 116 results in a large deflection of the needle depth limiter 112. The adjusting component 118 of the depth estimator mechanism 106 can take the form of a pulley system constructed from coaxial compound disks 232 connected by cables 234. The ratio of the disk diameters (i.e., the diameter of the large disk 236 divided by the diameter of the small disk 238) is the amplification factor for converting the upward motion of the compression sleeve 116 to the determined position of the needle depth limiter 112. This device can also be any type of mechanical or electromechanical element that converts upward motion to downward deflection with adjustable sensitivity. The connector component 120 can connect the cable 234 of the small disks 238 to the compression sleeve 116 such that movement of the compression sleeve 116 causes the adjusting component 118 to convert an upward thrust of the compression sleeve into a downward deflection of the needle depth limiter 112. The disk diameter ratio provides a fixed amplification between the compression sleeve movement and the needle depth limiter movement.

The sensitivity of the adjusting component 118 is adjusted by switching in different sets of disks to vary the sensitivity (or the amplification factor). The sensitivity adjustment can be used to adjust needle penetration parameters according to individual user classification (adult, pediatric, obese, etc.). This can be controlled by the position of the switch 132, which can select the amplification of the system by changing the set of disks 236/238 being used. A clutch mechanism 240 can be used to permit the rapid switching of from one sensitivity setting to another (disk to disk). Initially, the clutch mechanism 240 can be disengaged until the sensitivity setting is selected by the user. Once selected, the clutch mechanism 240 can engage and the appropriate disk ratio (sensitivity) can be used to set needle depth. In some implementations, the needle 108 can be preset for deployment at a predefined penetration depth. The adjusting component 118 may then adjust the penetration depth only if movement of the compression sleeve 116 indicates that it is needed (e.g., when the predefined penetration depth is not sufficient).

The switch 132 can also be used to set a metering valve 242 to adjust the amount of administered drug dispensed from a tank 244 storing the drug to match the user classification set by the switch (e.g., adult, pediatric, obese, etc.). The switch position can determine the dose supplied to the needle 108 from the tank 244 for injection. In addition to the use of adjustable, compound disks 236 and 238 to change depth sensitivity, other methods may be used. For example, a rack and pinion gear can be used to adjust the sensitivity over a range of ratios. This device can also be any type of mechanical or electromechanical element that converts upward motion to downward deflection with adjustable sensitivity. Adjustable sensitivity can permit the use of the same physical auto-injector device 100 with adults and children (as the maximum needle penetration in these two populations is different) or different body areas.

Figure 6:
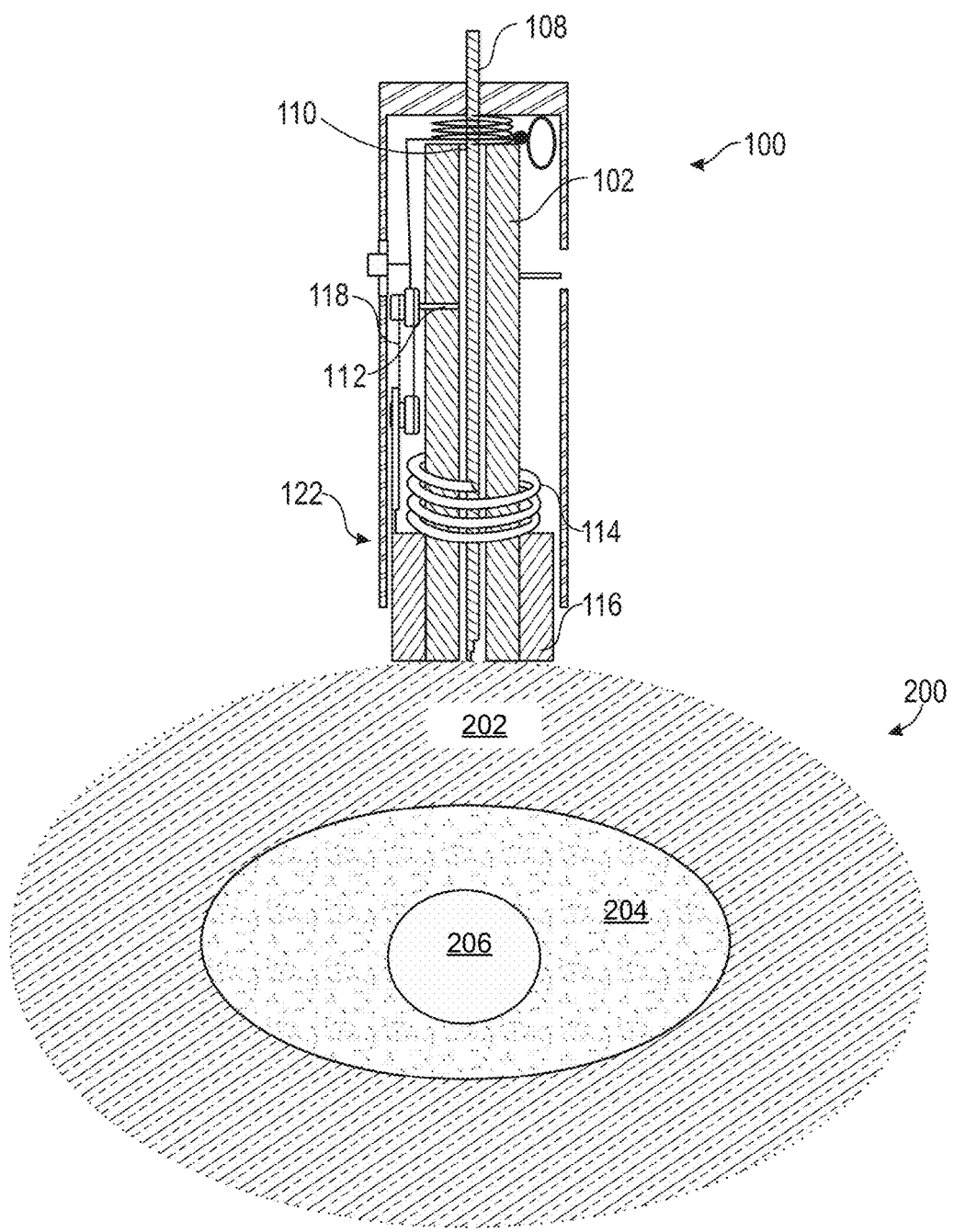
FIG. 6 is a drawing of an example of a cross section of the auto-injector device of FIG. 5 during use as compressed against a target area according to various embodiments of the present disclosure.

During use, the auto-injector device 100 is placed on a target area 200 where the compression sleeve 116 of the compression mechanism 104 is touching the target area 200. The target area 200 includes a fat region 202, a tissue region 204, and a bone region 206 as shown in FIG. 6. Since the auto-injector device 100 is not being pressed onto the target area 200, the compression sleeve 116 does not have an upward force applied to it and is not compressed upward, thus the needle depth limiter 112 is in the originally set and calibrated position.

Referring next to FIG. 6, shown is an example of the auto-injector device 100 following the deployment of the needle. The compression sleeve 116 of the compression mechanism 104 has moved upward about the needle housing 102 upon compression with the target area 200. Based upon the adjustment, the depth of the needle 108 is within the tissue region 204 of the target area 200 allowing for appropriate release of fluid into the tissue region 204.

As an alternative to the mechanical means of determining the thickness of the subcutaneous fat layer 202 and the setting of the appropriate penetration depth, a mini-ultrasound transducer located in the injector tip and connected to processing circuitry including a microprocessor may be used. Fat, muscle and bone have very different ultrasound signatures, thus the signals from the transducer can be processed by the microprocessor to determine the subcutaneous fat thickness and then set the needle depth limiter appropriately.

Figure 7:
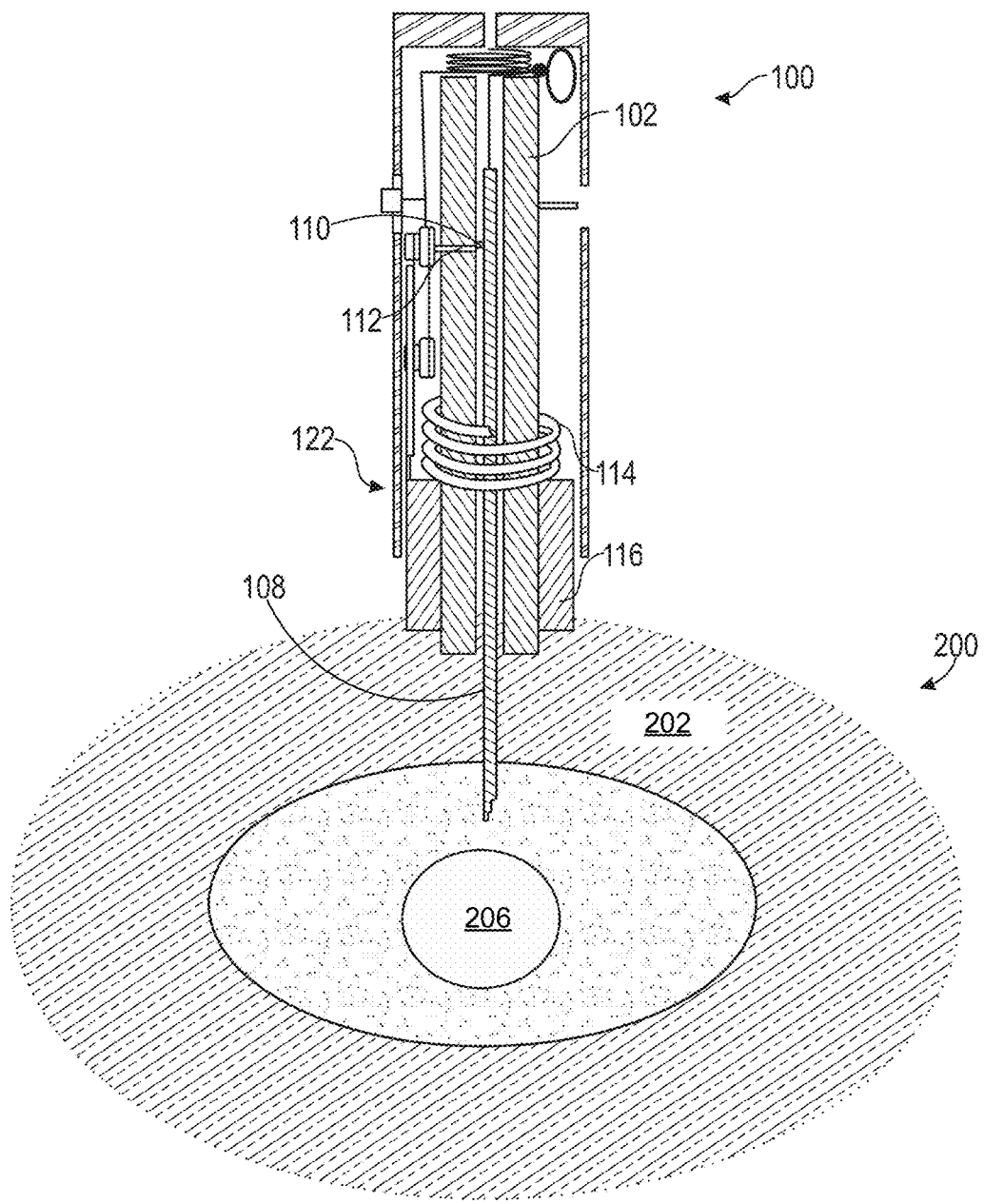
FIG. 7 is a drawing of an example of a cross section of the auto-injector device of FIG. 5 during use as compressed against the target area according to various embodiments of the present disclosure.

FIG. 7 shows an example of the auto-injector device 100 being activated within a target area 200. The adjusting component 118 can be calibrated to adjust the needle depth limiter 112 so the needle insertion depth will pass through subcutaneous fat 202 and penetrate muscle 204. The needle penetration depth is controlled so that it will not strike bone 206.

Prototype Testing

Figure 8:
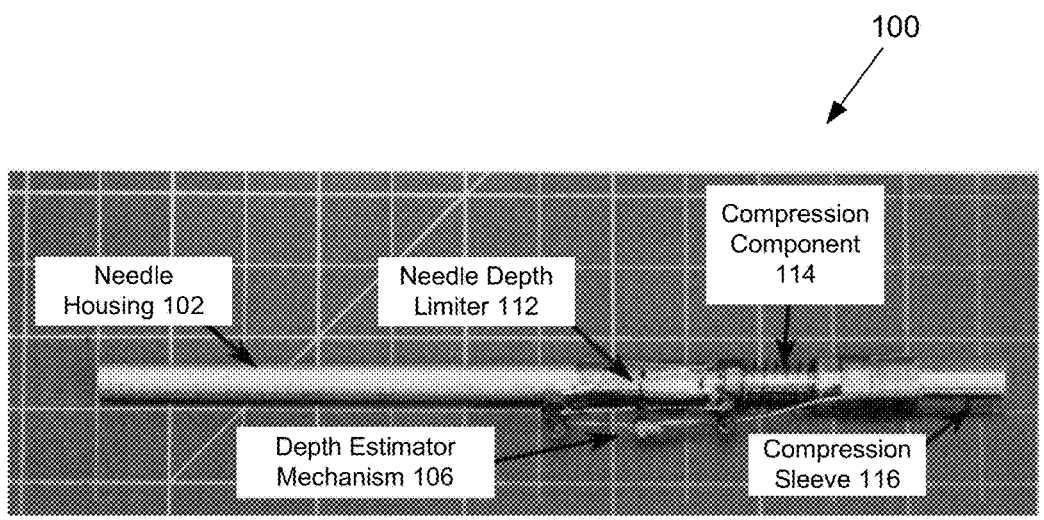
FIG. 8 is an image of an example of a prototype of the auto-injector device of FIG. 1 according to various embodiments of the present disclosure.

To test the auto-injector device 100 of FIG. 1, an engineering prototype was constructed to demonstrate the concept of compression adjustment of needle penetration depth. FIG. 8 illustrates an example of the auto-injector device 100 according to various embodiments of the present disclosure. The auto-injector device 100 of FIG. 8 comprises a needle housing 102 comprising an aluminum rod, a compression sleeve 116 comprising an acrylic tube, a compression component 114 disposed around the needle housing 102 and positioned at a distal end of the compression sleeve 116, and a depth estimator mechanism 106 comprising wax twine in a looped configuration positioned about two pulley components that are coupled to the needle housing 102.

The deflection of the needle depth limiter 112 as a function of hardness of the material in contact with the front of the auto-injector device 100 was assessed by placing three objects of different hardness beneath auto-injector device 100. For each experiment, a constant force was applied to the needle housing 102 by placing a 225 gram (g) piece of aluminum rod on top of the needle housing 102.

Figure 9A:
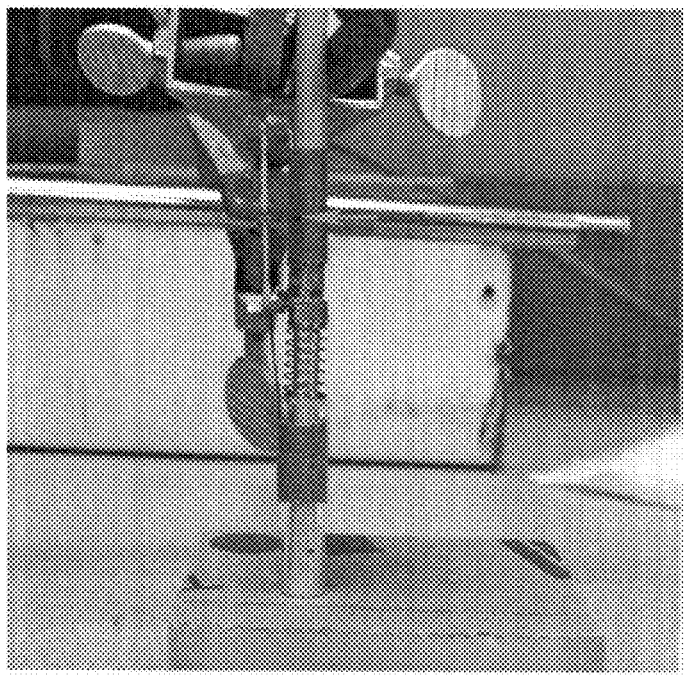
FIGS. 9A-9C are examples of the prototype auto-injector device of FIG. 8 being compressed on various objects according to various embodiments of the present disclosure.

The first object tests comprised a solid piece of acrylic. FIG. 9A illustrates an example of the auto-injector device 100 of FIG. 8 being pressed on the acrylic material. As shown in FIG. 9A, the needle depth limiter 112 does not move from its uncompressed position.

Figure 9B:
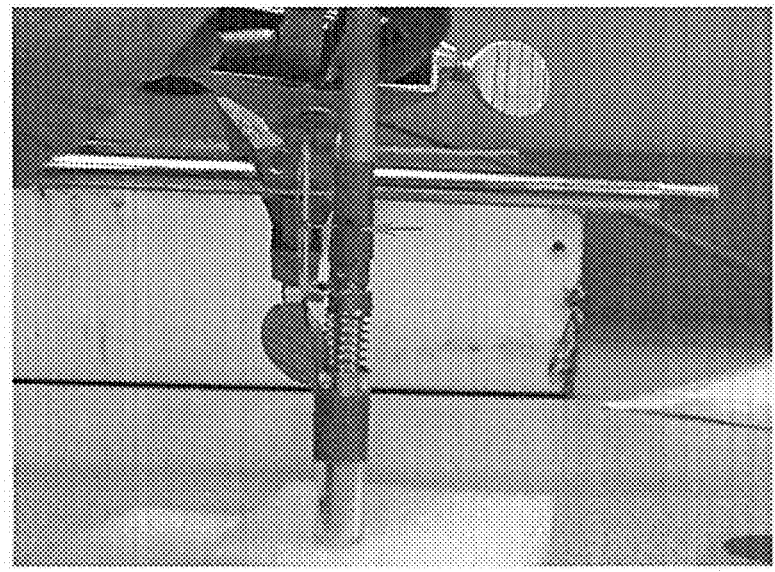

The next object tested comprised a stiff piece of foam. The stiff foam material was placed beneath the auto-injector device 100 and the 225 g aluminum rod was placed on the top of the needle housing 102 to provide the constant force. FIG. 9B illustrates an example of the auto-injector device 100 of FIG. 8 being used on the stiff foam material according to various embodiments of the present disclosure. As shown in FIG. 9B, deflection of the needle depth limiter 112 illustrates the needle housing 102 penetrated in the foam.

Figure 9C:
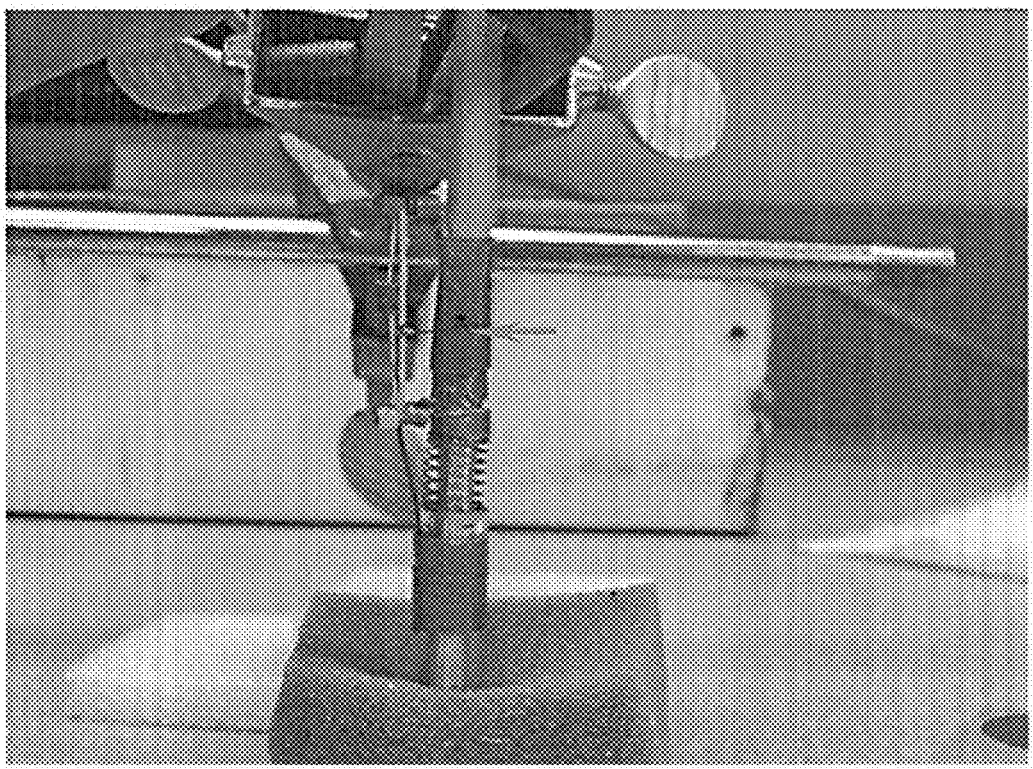

The final object tested comprised a softer piece of foam. The soft foam material was placed beneath the auto-injector device 100 of FIG. 8 and the 225 g aluminum rod was placed on the top of the needle housing 102 to provide the constant force. FIG. 9C illustrates an example of the auto-injector device 100 of FIG. 8 being used on the foam material according to various embodiments of the present disclosure. As shown in FIG. 9C, the limiter deflection was greater compared to the deflection for the stiff foam, demonstrating the greater compression of the softer foam (e.g., fatty tissue) compared to the stiffer foam (e.g., less fatty tissue). In various embodiments, the amplitude of the deflection can be adjusted by changing the spring constant of the compression component 114.

Figure 10:
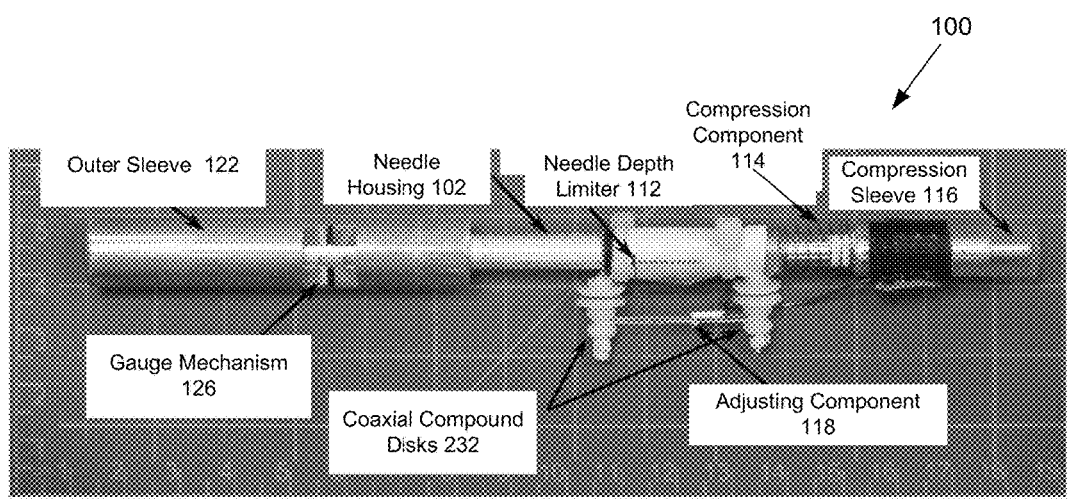
FIG. 10 is an image of an example of a prototype of the auto-injector device of FIG. 5 according to various embodiments of the present disclosure.

To test the auto-injector device 100 of FIG. 5, an engineering prototype was constructed to demonstrate the concept of compression adjustment of needle penetration depth. FIG. 10 illustrates an example of the auto-injector device 100 of FIG. 5 according to various embodiments of the present disclosure. The auto-injector device 100 of FIG. 10 comprises an outer sleeve 122 that a user can hold during deployment of the auto-injector device 100, a needle housing 102 comprising an aluminum rod, a compression sleeve 116 comprising an acrylic tube, a compression component 114 disposed around the needle housing 102 and positioned at a distal end of the compression sleeve 116, a needle depth limiter 112, a gauge mechanism 126, and an adjusting component 118 comprising compound disks 232 for adjustment of the deflection sensitivity.

Figures 11A, 11B:
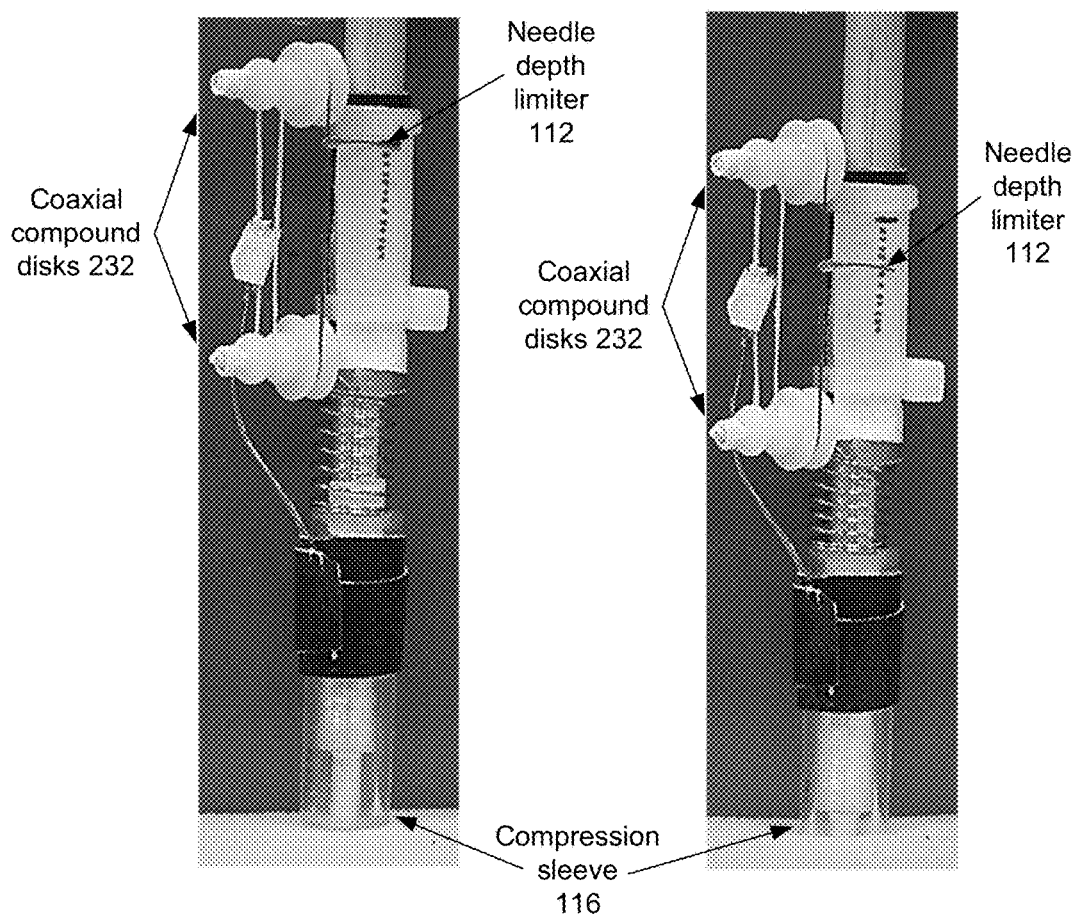
FIGS. 11A and 11B are images an example of a prototype of the auto-injector device of FIG. 5 according to various embodiments of the present disclosure.

FIGS. 11A and 11B illustrate an example of the auto-injector device 100 of FIG. 10 with compound disks for sensitivity adjustment. FIGS. 11A and 11B demonstrate the response of the prototype system to application of compression force. FIG. 11A shows the auto-injector device 100 (without the outer sleeve 122) in the rest position. FIG. 11B shows the auto-injector device 100 under compression, as indicated by the deflection of the needle depth limiter 112. Specifically, as the compression sleeve 116 is deflected upward, the needle limiter 112 moves down, which would be used to set the depth of the needle 108. The magnitude of deflection is related to the softness of the target area material in contact with the compression sleeve 116 of the auto-injector device 100.

Figure 12:
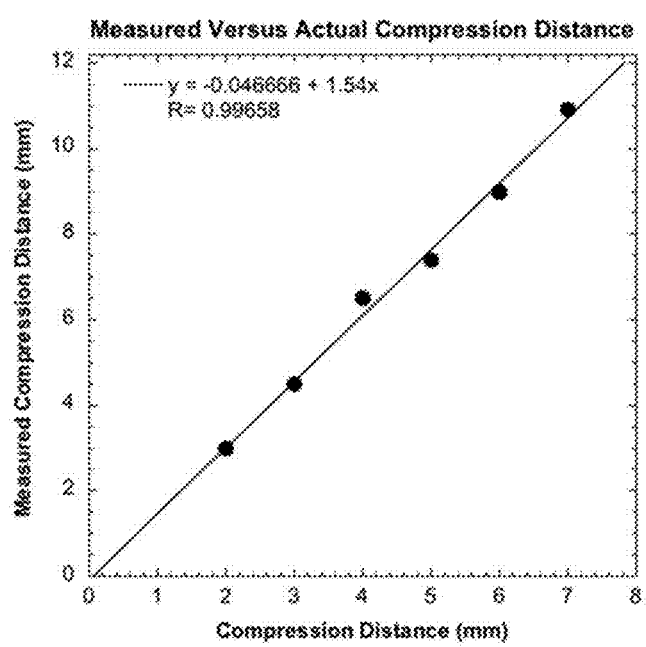
FIG. 12 is a plot illustrating an example of the deflection of the needle depth limiter as a function of the deflection of the compression sleeve of the prototype of FIGS. 11A and 11B according to various embodiments of the present disclosure.

The amplification factor produced by arrangement of the compound disks 232 used to construct the adjusting component (or thrust converter) 118 was determined by applying a known displacement to the compression sleeve 116 and measuring the resulting deflection of the needle depth limiter 112. FIG. 12 shows a plot of the deflection of the needle depth limiter 112 as a function of the deflection of the compression sleeve 116. A fit of the measured needle depth limiter motion versus the compression sleeve deflection data to a straight line shows that the y-intercept is about zero and the slope of the line is 1.54, which corresponds to the amplification factor of the system. The predicted slope, based on the ratio of the diameters of the large disk 236 to the small disk 238 was 1.6, which is in good agreement with the measured value of 1.54. This test demonstrated the ability to control the sensitivity of the depth measurement apparatus, and hence, the dynamic range of the needle depth adjustment. This capability allows the proper sensitivity to be set for optimal use.

Advantages of the auto-injector device 100 with an adjustable depth include:

The adjustable amplification of the auto-injector device 100 for converting upward to downward position permits optimization of the auto-injector device 100 operation during the calibration process.

Adjustable amplification enables the capability for the user to adjust sensitivity of the auto-injector device 100 for use with either an adult or a child.

The adjustable amplification can increase the choice of areas of the body where an auto-injector device 100 can be used. By changing the amplification with an external switch 132, the relationship between the deflection of the compression sleeve 116 and the needle depth can be adjusted to reflect the normal fat pad thickness expected in the target area 200, permitting the use of a single auto-injector device 100 for multiple (or selectable) body areas.

In addition to the foregoing, the various embodiments of the present disclosure include, but are not limited to, the embodiments set forth in the following clauses.

Clause 1. An auto-injector device, comprising: a needle; a needle housing, the needle being moveably disposed within the needle housing; a compression mechanism (such as a spring) surrounding a lower portion of the needle housing; and a needle depth estimator coupled to compression mechanism, the needle depth estimator comprising a needle depth limiter extending into an inner portion of the needle housing and being designed to engage with a needle stop of the needle and restrict downward movement of the needle, and the needle depth estimator being designed to automatically adjust a position of the needle depth limiter within the needle housing based at least in part on movement of the compression mechanism about the needle housing.

Clause 2. The auto-injector device of clause 1, wherein the compression mechanism comprises a compression tube and a spring, the spring being adjacent to a top end of the compression tube.

Clause 3. The auto-injector device of clause 2, wherein the compression mechanism creates a force that limits an upward movement of the compression tube about the needle housing.

Clause 4. The auto-injector device of clause 1, wherein an upward movement of the compression mechanism about a longitudinal axis of the needle housing causes the needle depth limiter to move in a downward direction about the longitudinal axis of the needle housing.

Clause 5. The auto-injector device of clause 1, wherein compression of a bottom end of the compression mechanism on a surface corresponds to a level of softness of the surface.

Clause 6. The auto-injector device of clause 5, wherein a needle depth of the needle penetrating the surface is based at least in part on an estimation of the level of softness.

Clause 7. The auto-injector device of clause 1, wherein the needle depth estimator comprises an adjustment component that moves the position of the needle depth limiter in a direction opposite of the direction of movement of the compression mechanism in response to the movement of the compression mechanism Clause 8. The auto-injector device of clause 1, wherein the needle depth estimator comprises a deflection sensitivity adjustment.

Clause 9. The auto-injector device of clause 8, wherein the deflection sensitivity adjustment comprises a pulley system constructed from coaxial compound disks connected by cables.

Clause 10. The auto-injector device of claim 8, wherein the deflective sensitivity adjustment comprises a mechanical or electromechanical element configured to convert upward motion to downward deflection with adjustable sensitivity.

Clause 11. The auto-injector device of clause 8, comprising a switch configured to select a sensitivity amplification factor for the deflection sensitivity adjustment.

Clause 12. The auto-injector device of clause 11, wherein the switch is configured to select a dosage amount of a drug that is dispensed through the needle.

Clause 13. The auto-injector device of clause 11, wherein the switch comprises fixed settings for predefined user classifications.

Clause 14. The auto-injector device of clause 1, comprising a gauge mechanism configured to monitor an amount of downward force exerted by a user of the auto-injector device and provide a feedback indication of the amount of downward force.

Clause 15. An auto-injector device comprising: a first tube; a second tube being moveably disposed around the first tube in a telescoping arrangement, the second tube being situated about a lower portion of the first tube; a compression component disposed around the first tube and being adjacent to a top end of the second tube, the compression component being designed to create a force that limits an upwards movement of the second tube about the first tube;

and a depth estimation mechanism coupled to the second tube, the depth estimation mechanism comprising a position indicator extending into an inner portion of the first tube, and the depth estimation mechanism being designed to adjust a position of the position indicator based at least in part on movement of the second tube.

Clause 16. The auto-injector device of clause 15, wherein the upwards movement of the second tube about the first tube causes the position indicator to move in a downward direction about a longitudinal axis of the first tube.

Clause 17. The auto-injector device of clause 15, wherein the first tube is a needle housing, and further comprising a needle being disposed within the needle housing.

Clause 18. The auto-injector device of clause 17, wherein the needle comprises a needle stop extending outwardly from an upper portion of the needle.

Clause 19. The auto-injector device of clause 18, wherein engagement of the needle stop with the position indicator restricts a downward movement of the needle about a longitudinal axis of the first tube.

Clause 20. The auto-injector device of clause 17, wherein compression of a bottom end of the second tube on a target area corresponds to a level of softness of the target area, and a needle depth of the needle penetrating the target area is determined based at least in part on the level of softness.

Clause 21. The auto-injector device of clause 15, wherein the depth estimation mechanism comprises an adjustment component that converts an upward thrust associated with the second tube into a downward deflection of the position indicator.

Clause 22. The auto-injector device of clause 21, wherein the adjustment component comprises a material looped about one or more pulley components along a longitudinal axis of the first tube, the material comprising at least one of twine, a string, a rope, a cord, a cable, or a wire.

Clause 23. The auto-injector device of clause 21, wherein the adjustment component comprises a mechanical or electromechanical element that converts upward motion to downward deflection with adjustable sensitivity.

Clause 24. The auto-injector device of clause 15, further comprising an outer sleeve disposed about the telescoping arrangement of the first tube and the second tube, wherein a force applied to the top of the outer sleeve by a user is transmitted via the outer sleeve to the first tube.

Clause 25. The auto-injector device of clause 24, wherein a determination of whether the force exceeds a force threshold corresponding to a sufficient needle insertion is based at least in part on a deflection of the outer sleeve.

Clause 26. The auto-injector device of clause 25, further comprising an indicator mechanism designed to indicate to the user whether the force applied corresponds to the sufficient needle insertion.

Clause 27. The auto-injector device of clause 25, wherein needle deployment is prevented in response to the force threshold not being exceeded.

Clause 28. The auto-injector device of clause 24, wherein needle insertion depth is further based in part on the force applied to the outer sleeve.

Clause 29. The auto-injector device of clause 24, wherein auto needle deployment occurs upon detection of a sufficient applied force.

Clause 30. The auto-injector device of clause 15, wherein the depth estimation mechanism comprises a deflection sensitivity adjustment.

Clause 31. The auto-injector device of clause 30, comprising a switch configured to select a sensitivity amplification factor for the deflection sensitivity adjustment.

Clause 32. The auto-injector device of clause 31, wherein the switch is configured to select a dosage amount for dispensation by the auto-injector device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. An auto-injector device, comprising:
a needle;
a needle housing, the needle being moveably disposed within the needle housing;
a compression mechanism comprising a spring coupled adjacent to a top portion of a compression sleeve, the compression mechanism surrounding a lower portion of the needle housing; and
a needle depth estimator coupled to the compression sleeve of the compression mechanism, the needle depth estimator comprising a pulley system and an arm coupled to and being substantially perpendicular to the pulley system, the arm extending from the pulley system and into an inner portion of the needle housing and being designed to engage with a needle stop of the needle and restrict downward movement of the needle, and the needle depth estimator being designed to automatically adjust a position of the arm within the needle housing based at least in part on movement of the compression mechanism about the needle housing.

2. The auto-injector device of claim 1, wherein the spring being designed to create a force that limits an upward movement of the compression sleeve about the needle housing.

3. The auto-injector device of claim 1, wherein an upward movement of the compression sleeve about a longitudinal axis of the needle housing causes the arm of the needle depth estimator to move in a downward direction about the longitudinal axis of the needle housing.

4. The auto-injector device of claim 1, wherein a needle depth of the needle penetrating a surface is based at least in part a level of softness of the surface.

5. The auto-injector device of claim 1, wherein the pulley system of the needle depth estimator is designed to move the position of the arm in a direction opposite of the direction of movement of the compression sleeve in response to the movement of the compression sleeve.

6. The auto-injector device of claim 1, wherein the needle depth estimator comprises a device configured to convert upward motion to downward deflection.

7. The auto-injector device of claim 1, comprising a switch configured to select a sensitivity amplification factor for the needle depth estimator.

8. The auto-injector device of claim 7, wherein the switch is configured to select a dosage amount of a drug that is dispensed through the needle.

9. The auto-injector device of claim 1, comprising a gauge mechanism configured to monitor an amount of downward force exerted by a user of the auto-injector device and provide a feedback indication of the amount of downward force.

10. An auto-injector device comprising:
a first tube;
a second tube being moveably disposed around the first tube in a telescoping arrangement, the second tube being situated about a lower portion of the first tube;
a spring disposed around the first tube and being adjacent to a top end of the second tube, the spring being designed to create a force that limits an upwards movement of the second tube about the first tube; and
a depth estimation mechanism coupled to the second tube, the depth estimation mechanism comprising a pulley system and an arm coupled to the pulley system and being substantially perpendicular to the pulley system, the arm extending into an inner portion of the first tube, and the depth estimation mechanism being designed to adjust a position of the arm based at least in part on movement of the second tube.

11. The auto-injector device of claim 10, wherein the first tube is a needle housing, and further comprising a needle being disposed within the first tube, and engagement of a needle stop of a needle with the arm restricts a downward movement of the needle about a longitudinal axis of the first tube.

12. The auto-injector device of claim 11, wherein compression of a bottom end of the second tube on a target area corresponds to a level of softness of the target area, and a needle depth of the needle penetrating the target area is determined based at least in part on the level of softness.

13. The auto-injector device of claim 10, wherein the pulley system is configured to convert an upward thrust associated with the second tube into a downward deflection of the arm.

14. The auto-injector device of claim 13, wherein the pulley system comprises a material looped about one or more pulley components along a longitudinal axis of the first tube.

15. The auto-injector device of claim 10, further comprising an outer sleeve disposed about the telescoping arrangement of the first tube and the second tube, wherein a force applied to the top of the outer sleeve by a user is transmitted via the outer sleeve to the first tube.

16. The auto-injector device of claim 15, wherein a determination of whether the force exceeds a force threshold corresponding to a sufficient needle insertion is based at least in part on a deflection of the outer sleeve.

17. The auto-injector device of claim 16, further comprising an indicator mechanism designed to indicate to the user whether the force applied corresponds to the sufficient needle insertion.

18. The auto-injector device of claim 15, wherein needle insertion depth is further based in part on the force applied to the outer sleeve.

19. The auto-injector device of claim 10, wherein the depth estimation mechanism comprises a deflection sensitivity adjustment, and further comprising a switch configured to select a sensitivity amplification factor for the deflection sensitivity adjustment.

20. The auto-injector device of claim 19, wherein the switch is configured to select a dosage amount for dispensation by the auto-injector device.

* * * * *